(12) United States Patent
Coleman et al.

(10) Patent No.: US 7,943,175 B2
(45) Date of Patent: May 17, 2011

(54) CALIXARENE BASED DISPERSIBLE COLLOIDAL SYSTEMS IN THE FORM OF NANOPARTICLES

(75) Inventors: Anthony Coleman, Caluire (FR); Philippe Jean-Boris Goreloff, Saint Maurice de Beynost (FR)

(73) Assignee: Nanoport S.A. (CH)

( * ) Notice: Subject to any disclaimer, the term of this patent is extended or adjusted under 35 U.S.C. 154(b) by 881 days.

(21) Appl. No.: 10/489,894

(22) PCT Filed: Sep. 11, 2002

(86) PCT No.: PCT/EP02/10169
§ 371 (c)(1),
(2), (4) Date: Mar. 17, 2004

(87) PCT Pub. No.: WO03/024583
PCT Pub. Date: Mar. 27, 2003

(65) Prior Publication Data
US 2005/0084535 A1    Apr. 21, 2005

(30) Foreign Application Priority Data

Sep. 17, 2001 (EP) ................................. 01122184

(51) Int. Cl.
*A61K 9/14* (2006.01)
*A61K 8/02* (2006.01)

(52) U.S. Cl. .................. 424/489; 424/401; 424/484

(58) Field of Classification Search .................. None
See application file for complete search history.

(56) References Cited

U.S. PATENT DOCUMENTS

| 3,565,887 A | | 2/1971 | Parmerter et al. | |
| 5,622,687 A | * | 4/1997 | Krishnan et al. | 424/9.33 |
| 5,718,905 A | * | 2/1998 | Skiba et al. | 424/499 |
| 5,854,225 A | | 12/1998 | Richard et al. | |
| 6,423,547 B1 | * | 7/2002 | Rajagopalan et al. | 424/9.6 |
| 2004/0229039 A1 | * | 11/2004 | Wei et al. | 428/403 |

FOREIGN PATENT DOCUMENTS

| EP | 0646002 | | 4/1995 |
| EP | 954965 A1 | * | 11/1999 |
| FR | 2681868 | | 4/1993 |
| JP | 6043573 | | 2/1994 |
| WO | WO 9325195 A1 | * | 12/1993 |
| WO | WO 9731698 A1 | * | 9/1997 |

OTHER PUBLICATIONS

Atsushi Ikeda et al. "Water-soluble [60] fullerene-cationic homooxacalix[3]arene complex which is applicable to the photocleavage of DNA" *Chemical Communications* 1999, pp. 1403-1404; Royal Society of Chemisty, GB.

Shahgaldian, et al., "Synthesis and properties of novel amphiphilic calix-[4]-arene deriavtives" *Tetrahedron Letters 42* (2001) 577-579.

"A First Approach to the Study of Calixarene Solid Liquid Nanoparticle (SLN) Toxicity" Patrick Shahgaldian, Eric da Silva and Anthony W. Coleman; Journal of Inclusion Phenomena and Macrocyclic Chemistry 46: 175-177, 2003.

\* cited by examiner

*Primary Examiner* — S. Tran
(74) *Attorney, Agent, or Firm* — Ostrolenk Faber LLP

(57) ABSTRACT

A water dispersible colloidal system in the form of generally spherical matrix type particles and of sizes typically in the range of from 50 to 500 nm, called nanoparticles, and a process for the preparation of such systems. The system is characterized in that the nanoparticles comprise at least one amphiphilically modified calixarene. The water dispersion contains at least one active component such as a cosmetic, a pharmaceutical compound or other biologically active substances, foods, beverages, etc. enclosed within the nanoparticles, in the outer aqueous phase, or in both. The systems show outstanding properties, especially long-life stability even at elevated la temperatures.

21 Claims, No Drawings

CALIXARENE BASED DISPERSIBLE COLLOIDAL SYSTEMS IN THE FORM OF NANOPARTICLES

FIELD OF THE INVENTION

The present invention relates to a novel amphiphilic calixarene based water dispersible colloidal system in the form of generally spherical matrix type particles and of sizes typically in the range of from 50 to 500 nm. These particles are called in the following "solid nanospheres, and they are capable of encapsulating and transporting one or more active molecules. They are generally prepared under varying ionic forces of salts, and at varying pH and temperatures. The invention further relates to processes for the preparation of this system.

BACKGROUND OF THE INVENTION

It is already well known to the one skilled in the art that relatively small molecules can be captioned by larger molecules which may be monomeric or polymeric, having an intramolecular or an intermolecular cavity. The size of such combinations of at least two different molecules, the host molecules containing guest molecules, is in the submicron range as mentioned above, namely between 50 and 500 nanometers.

Submicron particles are for example disclosed in the following patents: BE-A-808,034, BE-A-839,748, BE-A-869,107, FR-A-2,504,408, EP-A-0,275,796, EP-A-0,349,428, U.S. Pat. No. 5,718,905, WO93/25,194 and FR-A-2,681,868.

Belgian Patents No. 808,034 and 839,748 describe submicron particles formed by polymerization of monomers including acrylic or methacrylic acid derivatives. Micellar and/or interfacial polymerization of the various monomers generates particles of size under the micron scale. These systems may encapsulate active substances. The particles form stable aqueous colloidal suspensions allowing such the particles to carry biologically active molecules for medical administration. However, the high degree of stability and the lack of a suitable route for biological elimination of the polymeric acids give rise to a serious drawback in their use, in that they are retained within body tissue or within body cavities leading to possible side reactions.

This drawback is partially overcome according to patent BE-A-869,107 where biodegradable nanoparticles containing a biologically active molecule are cited. The polymers used are alkyl-cyanocrylate based copolymers of known biocompatibility. The main drawbacks of these systems arise from the toxicity of degradation products under physiological conditions as well as the methodology of the encapsulation of active substrates. Under the procedure described, a highly dense polymer lattice is the basis of the formation of the particles. Surface adsorption of molecules is used in the transport and hence incorporation levels are low. Secondary problems arise from the control of the polymerization reaction, which may leave either soluble monomers or soluble short oligomers, and these compounds may subsequently be leached from the matrix. The purification processes used are both highly time consuming and expensive.

Proteins, such as albumin, have been used to prepare nanosystems by thermal denaturing (Kramer, P. A. J., *Pharm. Sci.*, 63, 1646, 1974) or by salt or solvent denaturing of proteins such as gelatin in solution (Martey et al., *Aust. J Pharm. Sci.*, 6, 65, 1978 or *Pharm. Acta Helv.*, 1, 53, 1978). The denaturated protein dispersion are subsequently reticulated. In the first case, the need to pre-disperse the protein in an oil-water emulsion requires use of secondary surfactant and also sonication. In the second case large amounts of inorganic material must be removed prior to use. In both systems excess, toxic, aldehyde must be removed.

EP-A-0,275,796 and EP-A-0,349,428 disclose nanoparticles that are prepared by solvent diffusion methods from two non-miscible systems. However, the protein-based nanosystems described in EP-A-0,349,428 require the use of highly specific conditions, limiting their application.

French patent FR-A-2,551,072 describes micrometric capsules as a form of sustained-released pharmaceutical system, which are prepared from polyol esters. However, such microparticles are not suited to intravascular administration without entailing medical risk.

Several patents, such as U.S. Pat. No. 5,718,905, WO 93/25194 and FR-A-2,681,868 describe the use of modified cyclodextrins as base material for the nanospheres. They have the advantage of being biodegradable, their administration is followed by release of the active molecule, and it is possible to obtain biodegradability, which is suitably controlled by making use of modified cyclodextrins which differ from each other in the nature of the substituent groups used. Such modified cyclodextrins and the preparation thereof are especially described by Pin Zhang, C. C. Ling, A. W. Coleman, Parrot-Loppez and H. Galons in *Tetrahedron Letters* 32, No. 24, 2679-70, 1991.

However, all the cyclodextrin based nanosystems share a number of problems; firstly high cost of synthesis and production as the initial modifications all require a vacuum drying of the cyclodextrins at 120° C.; secondly the use of toxic reactive material, including pyridine, iodine, sodium azide, secondary alnines which may remain trapped in the molecular cavities; thirdly biodegradation may liberate the parent cyclodextrin known to be highly hemolytic. No evidence has been presented that this hemolytic activity is absent in the modified species.

SUMMARY OF THE INVENTION

The invention aims at eliminating all these problems and to provide a novel class of nanosystems of the above-depicted kind that are completely compatible with medical, biological, veterinary, cosmetic and alimentary use, which are easy and relatively inexpensive to manufacture from non-toxic compounds, which will not entrap toxic or incompatible compounds during manufacture, and which will neither yield toxic or even incompatible matter during biodegradation.

The nanoparticles according to the present invention comprise amphiphilically modified calixarenes as the enclosing molecules. The new compositions of the invention comprise a dispersible colloidal system composed of said nanoparticles as a carrier and of at least one active compound to be carried.

Calixarenes are polycyclic compounds that are known since the 1970's. A review of this class of chemical compounds may be found, e.g., in C. D. Gutsche, "Topics in Current Chemistry", Vol. 123, Springer 1984, p. 1 to 47; and C. D. Gutsche, "The calixarenes revisited", *Chem. Soc.*, 1998. Calixarenes are generally obtained from a para substituted phenol and an aldehyde, typically formaldehyde, and by cyclization of the linear oligomers that are primarily formed. They are extremely stable compounds and have already been proposed as confining materials for high toxic wastes due to their inertness, insolubility and thermal stability.

The invention further provides a process for the preparation of the new calixarene based composition. This process comprises the steps of (1) providing at least one amphiphilic substituted calixarene, (2) providing a liquid phase essentially consisting of a solution of said amphiphilic calixarene in an organic solvent, (3) providing a second liquid phase consisting of water or an aqueous mixture or ionic solution, (4) combining said two liquid phases of steps (2) and (3), and (5) recovering a colloidal suspension of nanospheres containing said amphiphilically substituted calixarene.

It is preferred to use in step (2) an organic solvent selected from oxygen containing compounds such as alcohols, ketones, aldehydes, ethers and mixtures thereof. The solvent may be a mixture of two or more solvents and may also contain water.

The combination of the two phases as per step (4) is preferably conducted under moderate stirring in pouring one of the two phases into the other.

The active material to be combined with the nanospheres is contained in at least one of the liquid phases described in steps (2) and (3) above, but preferably only in one of the two phases (2) or (3). This active material may be selected of at least one of the following materials and substances, given by way of example as a non-exhaustive listing, and belonging to the following groups:

A) Cosmetic substances: Oils, ointments, anti-oxydants, dyestuffs, vitamins, amino acids, peptides, proteins, salts, surfactants, hydrating compounds, emulsifiers, gels, soaps, essential oils, perfumes, dehydrating or desiccant agents, etc.;

B) Foods and beverages: oils, anti-oxydants, dyestuffs, vitamins, amino acids, peptides, proteins, salts, surfactants, hydrating compounds, emulsifiers, gels, flavoring agents, essential oils, smelling agents, sugars, lipids, sweetening agents, stabilizers, taste modifiers, volatile substances, etc.;

C) Phytosanitary products: fertilizers, insecticides, pesticides, acarizides, etc.; and D) Pharmaceuticals: medicines, medications, imaging agents, dyes, vitamins, amino acids, peptides, proteins, salts, nucleic acids and DNA, carbohydrates, lipids and phospholipids, etc.

Both phases (2) and (3) may contain auxiliary agents such as sturfactants, co-surfactants, stabilizers, dispersing agents, dyes, etc.

The nanoparticles are recovered as a colloidal suspension that is formed because the substituted calixarenes, dissolved in the organic phase (2), are virtually insoluble in the aqueous phase (3). Therefore, when preparing said two phases, care must of course be taken that the solvents used are selected in response to the solubility and insolubility, respectively, of the particular substituted calixarene that is used. Such considerations go without saying and are familiar to the one skilled in the art.

The substituted calixarenes that are preferably used in the practice of the present invention are described by the general formula Formula 1

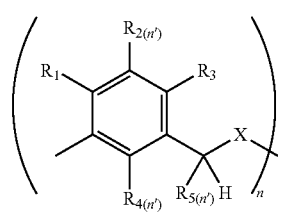

wherein:
$R_1$=H, OH, OR or OCOR;
$R_2$=H, R, COR, $CH_2Pol$, Y or $CH_2Y$;
$R_3$=H, OH, OR or OCOR;
$R_4$=H, OR, $OCH_2R$, OCOR or an ester, carboxylic acid, amido, amino, peptide or carbohydrate group;
$R_5$=R or Y;
R=a saturated or unsaturated straight or branched hydrocarbon chain that may be substituted by halogen and/or by a group Pol; or R is a cyclic hydrocarbon radical, saturated or not;
Pol=a polar group selected from phosphoric acid, sulfuric acid, amino, ammonium, carboxylic acid and their salts;
Y=halogen or pseudo-halogen;
X=a direct bond, O, S or $NR_6R_7$;
$R_6$=alkyl, acyl or hydrogen;
$R_7$=alkyl, acyl or hydrogen;
n=an integer of from 3 to 20; and
n'=an integer≦n;
the compound of the above formula containing at least one group Pol.

The compounds of formula 1 can be prepared, starting from well-known calixarenes, according to the method described by P. Shahgaldian, A. W. Coleman and V. I. Kalchenko in *Tetrahedron Letters* 42 (2001), 577-579, which is incorporated herein by reference.

The general feature of these molecules is that a hydrophobic function, generally an acyl or allcyl chain, is attached either at the phenolic oxygen or at the carbon atom situated in the para position to the hydroxyl function, although such hydrophobic groups may also be coupled onto the bridging substituent (carrying the radical $R_5$), and that a suitable hydrophilic function, namely one or more of the polar functions cited in formula 1, is attached at the opposing function to that modified by the hydrophobic function. The calix[n]arene may contain from 4 to 20 phenolic groups. The bridging function may be a simple methylene group, an oxo-methylene group, a bridging atom such as O, S, $NR_5R_6$, etc; or may be further branched. The invention allows to extend the possible calix[n]arene skeleton to the known calix-resorcinarenes, systems based on cluomotropic acid and heterocyclic structures having the same skeletal structure as the calix[n]arenes. Specific examples of such molecules are described in the publication of Felix et al. (*Tetrahedron Letters* 1998 vol 39, 9171); and Shahgaldian et al., already cited above.

Qptimal encapsulation of an added molecule is obtained by dissolving it in the phase in which it is soluble. The active molecules used here are those having known or potential cosmetic applications, including non exhaustively colorants, vitamins, essential oils, pro-vitamines, peptides, mono or pglysaccharides, proteins, hormones, etc.

The choice of the solvent system used in 1) may include alcohols such as methanol, ethanol, propanols, butanols, etc., ketones such as dimethylketone, ethylmethylketone, diethylketone, and the like, aldehydes such as acetaldehyde, propioaldehydes (branched or not), butyraldehydes (branched or not) and the like, ethers such as dimethyl ether, ethyl methyl ether, diethyl ether, tetrahydrofulan and the like. The choice of aqueous system in phase (3) may include pure water, ionic solutions in water, acid or base solutions, solutions of polar solutes including carbohydrates, alcohols, amino acids, etc. All these solutions may contain or not molecules having known potential cosmetic applications including vitamins, pro-vitamins, peptides, amino-acids, antioxidant molecules, dyes, aroma components, etc.

The process of the invention may be performed at various temperatures (which have little influence on the progress thereof), especially between 0° C. and the boiling temperature of the solvents. The volume ratio between phase (2) and phase (3) may preferably range from 0.1 to 1.

Where considered useful, one or more co-surfactants may be used in the preparation of the matrix nanospheres, these may include ionic surfactants such as carboxylic acids, allcylphosphonates, alkylsulfonates, allcylamines, nonionic surfactants such as pluronic acid, Tween etc.; their proportion may vary between 0.01% and 10%. The use of such co-surfactants has essentially zero effect on temporal stability but may allow the size of the matrix nanosphere to be varied.

The size of the matrix-based nanospheres of this invention can be varied by the selection of the speed of the addition of phase (2) to phase (3) or vice versa, of the concentrations of solid matter in the two phases, of and also by modification of the nature and/or the concentration of the calix[n]arene and the solvent used. It has also been found that in some cases, the temperature of the two phases had an influence on the size of the nanospheres that are obtained. The agitation of the mother solution requires a stirring that is sufficient to homogenize the mixture of the phase (2) and (3) and is best achieved by mechanical stirring for example using a magnetic rod at 50-500 rev/min. Stirring is not essential for the preparation of small quantities of nanospheres.

The surfactant mentioned above may be especially present in a proportion of from 0.1 to 10%, preferably from 0.2 to by weight of the colloidal suspension obtained in step (4). The colloidal suspension of nanospheres may be concentrated, sterilized, buffered (for example to physiological pH), centrifuged, dialyzed and freeze dried as required. For the nanospheres of this invention, the preparation has the advantage of being reversible. The colloidal system may be recreated by simple treatment with an aqueous solution.

A major and fully unexpected advantage of the present invention is the high temporal stability of the matrix nanospheres. They retain their original size and all their other physical properties over periods of more than 1 year even when maintained at 4°, 20° and 40° C.

The nanospheres described herein may be imaged by high resolution microscopy (either SEM/TEM microscopy or atomic force microscopy). The use of this mode to image the system clearly demonstrate the high mechanical stability of the system. This can be compared to the requirement of non-contact mode AFM imaging to visualize cyclodextrin based colloidal nanospheres. (Sommer et al., *Supramol. Chem.*, 1993, vol 3, 19). The nanospheres produced may be varied in size from 50 to 500 nm with general size between 90 and 200 nm. Such size variations are obtained by the technique cited above.

High, to very high, loading factors of incorporated molecules may be obtained using the calix[n]arene based nanospheres, for example loading factors of 1 to 25% may easily be obtained. Such loading in the matrix allows: a) transport of molecules insoluble in aqueous systems, b) protection of such molecules against degradation either by chemical or biological processes, c) modification of the kinetics of transport and availability of incorporated molecules in cosmetic applications.

Test have shown no apparent cytotoxicity or hemolytic effects of the calix[n]arene based nanospheres, the parent calix[n]arenes and the derivatives cited herein at the cellular level. (Perret, F., Shahgaldian, P. et al., *International Symposium on Supramolecular Chemistry*, Fukuoka, 2000).

The nanospheres of this invention may contain one or several active molecules within their matrix, for example retinal, β-carotene, menthol or other cosmetically applicable molecules. Details have been described above.

It is believed that the calixarene compounds confine the active matter (if this active matter is contained in the inner phase of the dispersion) according to two mechanisms: First, particles of said active matter are simply surrounded by a spherical shell of a calixarene network, but in addition, specific moieties of the active matter are retained by the molecular cavities of the calixarene molecules and/or are entrapped by secondary chemical or physical forces such a hydrogen bridges and van der Waals forces.

Accordingly, the active matter is rather solidly retained by the calixarene networks. Liberation of active matter is controlled by one or more of the following measures:

1) Raise of temperature: If the temperature of the nanodispersion is increased, e.g. to 60° C., the liberation of the active matter is increased.

2) Change of the pH value: If the pH is lowered, the speed of liberation is drastically increased. This is most probably due to the destruction of hydrogen bridge links between the calixarene and the active matter (see above) and to the break-up of the calixarene network. The pH may be lowered, where possible, until pH 3.0 to 2.5 or 2.0.

3) Environmental influences: When the dispersion is contacted with the environment to which the active maker should be applied, for example to the human skin if the dispersion is a cosmetic one and contains a cosmetically active substance, the secretions of the skin or the presence of certain amino acids in the proteins will accelerate the liberation of the active matter by chemical and/or physical attraction; the outer phase of the dispersion is altered, and the equilibrium of the dispersion is modified.

Generally, any change of the equilibrium of the dispersion will influence the liberation speed of the active matter.

On the other hand, the new calixarene based nanoparticles which are present as colloidal dispersions, have an unexpectedly high longtime stability in diluted salt solutions. For example, these dispersions are stable for more than 250 days at room temperature and at 40° C., in the presence of sodium sulfate, sodium acetate, sodium bicarbonate, potassium chloride, potassium dihydrophosphate and potassium iodide up to salt concentrations betwwen 10-4 and 10-2, in some cases up to 10-1 mol/l. An increase in particle size, which may be interpreted as a partial aggregation, is observed before the destruction of the colloid by precipitation.

As already mentioned above, the new dispersions of nanoparticles may be used in a wide variety of fields. Preferred are applications in cosmetics, medicine, agriculture (phytosanitary) and food industry. The toxicity of the new compositions has been tested according to three methods:

First, phosphorylated p-acylcalix[4]arenes were tested on human lymphoblast cells, using vinblastine as an active substance. Viability values between 91 and 97% have been found.

Second, p-dodecanoyl-calix[4]arene has been tested on embryo insect cells (*trichiopusia ni*). Viability values of more than 80% have been found.

Third, hemolytic tests have been conducted using five different p-acylcalix[4]arenes on human blood cells. The liberation of hemoglobin which indicates a hemolysis, has been determined. No presence of free hemoglobin has been detected in all five cases at calixarene concentrations between 15 and 150 mg/l at 37° C. during 30 minutes.

Thus, the complete absence of toxicity (the results of insect embryo cell tests cannot be taken as indicative for human cell toxicity but indicate an extraordinarily low toxicity per se) makes the new compositions fully compatible with preliminary requirements for medical and all other human use.

DETAILED DESCRIPTION OF THE INVENTION

The invention is illustrated by the following examples that are not construed to limit the invention in any way:

Part I. Preparation of P-Substituted Calixarenes

EXAMPLE A

Synthesis of Hexa-p-dodecanoyl-calix[6]arene

Under a nitrogen blanket, 3 g (4.7 mmol) of calix[6]arene, 7.2 g (7 val) of dodecanoyl chloride and 6.3 g (10 val) of anhydrous aluminum chloride are added under anhydrous conditions to 200 ml of dry nitrobenzene. the deep orange solution is stirred during 20 hours at room temperature. The reaction is then quenched by poring the reaction mixture on 1 kg of ice. the reaction product is extracted with chloroform, washed successively with 500 ml 1M hydrochloric acid, 2,500 ml of 1M NaCl solution, and 2,500 ml of deionized water. The organic phase is dried on magnesium sulfate, and the solvent is evaporated in vacuo until a final volume of 50 ml. The brownish orange residue is added to 500 ml of methanol, and the fine precipitate is filtered off and dried in vacuo. The white powder thus obtained is analyzed by NMR, and the structure of hexa-p-dodecanoyl-calix[6]arene is ascertained. Yield: 50%.

In modifying the amounts of the calixarene component, and by using the same reaction conditions and working techniques, other p-dodecanoyl-calixarenes and other p-acyl-calixarenes have been obtained in yields between 50 and 85%.

Part II. Preparation of the Nanosphere Compositions

EXAMPLE 1

Preparation of a Nanoparticle Dispersion

This Example illustrates the typical working technique for the manufacture of the compositions of this invention.

The preparation of calixarenes modified by coupling a 12 carbon atom acyl chain in the para position to phenolic hydroxyl function is for example described in Shahgaldian et al. (loc. cit.) See also Example A above.

Tetra-p-dodecanoyl-calix[4]arene is dissolved in a suitable solvent, in the case of this example tetrahydrofuran, to generate phase (2) (3 ml). Phase (2) is added to an aqueous phase is (3) (100 ml) under magnetic stirring. The medium immediately becomes opalescent by formation of modified calix [4]arene nanosphere. The average size of the nanospheres, measured by a laser-beam diffractometer (4700C from Malvern), is 150 nm with an average dispersion index of 0.1.

The suspension may be concentrated under reduced pressure to the desired volume, for example 10 ml or thereabouts.

The appearance of the nanosphere suspension remains unchanged after standing for a prolonged period (12 months) and there is no sign, in particular, either of irreversible sedimentation or of variation in the size of the nanospheres.

EXAMPLE 2 (Variant of Example 1)

The method is carried out as in Example 1, but by adding the aqueous phase (3) to the tetrahydrofuran phase (2). The nanosphere dispersion obtained has the same characteristics as those described in Example 1.

EXAMPLE 3 (Variant of Example 1)

The method is carried out as in Example 1, but by adding the tetrahydrofuran phase (0.5 ml) to the aqueous phase (10 ml) without stirring the medium. The nanospheres obtained are 145 nm in size and have an average dispersion index of 0.11.

EXAMPLE 4 (Variant of Example 1)

The method is carried out as in Example 1, but with addition of a surface-active agent (Tween, 0.1-1%, v/v) to the aqueous phase. The nanospheres obtained are 150 mn in size and have an average dispersion index of 0.3.

EXAMPLE 5

Sterile Preparation of Nanospheres

The method is carried out as in Example 1, and the obtained suspension of nanospheres is then sterilized in an autoclave at 120° C. for 15 minutes. The average particle size remains essentially unchanged after sterilization.

EXAMPLE 6

Freeze Drying Preparation of 12-Carbon Acyl Chain Modified Calix[4]arene Nanospheres The method is carried out as in Example 1, and the suspension is then freeze-dried. The addition of a cryoprotector (maltose, trehalose and the like) is not essential. The average particle size measured immediately after freeze-drying remains unchanged.

EXAMPLE 7

Preparation of Para-Galactosyl-O-5-Carbon Modified Calix[4]arene Nanospheres

The method is carried out as in Example 1, replacing 12-carbon acyl chain modified calix[4]arene by para-galactosyl-O-5-carbon modified calix[4]arene. The average size of the nanospheres is 110 nm with an average dispersion index of 0.1.

These nanospheres may be sterilized in the autoclave and freeze-dried as for those cited in Example 1.

EXAMPLE 8

Preparation of 12-Carbon Acyl Chain Modified Calix[6]arene Nanospheres

The method is carried out as in Example 1, replacing the respective calix[4]arene derivative with a calix[6]arene derivative containing 6 phenolic units. The average size of the nano-spheres formed is 145 nm with a high polydispersity index of 0.21.

EXAMPLE 9

Preparation of 12-Carbon Acyl Chain Modified Calix[8]arene Nanospheres

The method is carried out as in Example 1, replacing the respective calix[4]arene derivative with a calix[8]arene derivative containing 8 phenolic units. Under these conditions stable nanospheres were also obtained.

EXAMPLE 10

Preparation of Mixed 12-Carbon Acyl Chain Modified Calix[n]arene Nanospheres, Where n=4, 6 and 8

The method is carried out as in Example 1, replacing the respective calix[4]arene derivative with a mixture of 12-carbon acyl chain modified calix[n]arenes, in the proportions 1:1 for binary mixtures and 1:1:1 and 1:1:2 for tertiary mixtures.

TABLE 1

Diameter and polydispersity index for suspensions of mixed nanospheres (1: para-dodecanoyl-calix[4]arene, 2: para-dodecanoyl-calix[6]arene, and 3: para-dodecanoyl-calix[8]arene).

| Proportion in 1 | Proportion in 2 | Proportion in 3 | Diameter in nm | Polydispersity Index |
|---|---|---|---|---|
| 1/3 | 1/3 | 1/3 | 122 | 0.31 |
| 1/2 | — | 1/2 | 176 | 0.26 |
| — | 1/2 | 1/2 | 140 | 0.25 |
| 1/2 | 1/4 | 1/4 | 155 | 0.20 |
| 1/4 | 1/4 | 1/2 | 140 | 0.37 |

EXAMPLE 11

Stability of the Calix[4]arene Nanospheres in the Presence of Variable Ionic Strengths The method is carried out as indicated in Example 1. After concentration of the suspension of modified-calix[4]arene nanospheres to a volume of 10 ml, increasing quantities of sodium chloride are added thereto. The nanosphere suspension is perfectly stable when the sodium chloride concentration corresponds to physiological ionic strength (0.154 M) and stability remains at concentrations up to one order of magnitude greater than physiological ionic strength.

EXAMPLE 12

Stability of the Calix[n]arene Nanospheres in the Presence of an Acidic or Basic Medium The method is carried out as indicated in Example 1. After concentration of the suspension of calixarene nanospheres to a volume of 10 ml., increasing quantities of hydrochloric acid (1 mole per liter) or of sodium hydroxide (1 mole per liter) are added progressively to the medium. The nanosphere suspension is perfectly stable, under pH values ranging from 1 to 12.

EXAMPLE 13

Temperature-Stability of the Calix[n]arene Nanosphere

The method is carried out as indicated in Example 1. After concentration of the suspension of calix[n]arene nano spheres to a volume of 30 ml, three batches of 10 ml each are prepared. The batches are placed at 3° C., 20° C. and 40° C., respectively. The suspensions remain stable over time and do not exhibit, after storage for a minimum of 12 months, either irreversible sedimentation or variation in the size of the nanospheres.

EXAMPLE 14

Preparation of Nanospheres in the Presence of a Salt

The method is carried out as indicated in Example 1, in this case a 0.154 mole/liter solution of sodium chloride is used as phase (3). The nanospheres prepared under physiological ionic strength have a size of 160 nm with a dispersion index of 0.15 nm.

The suspension remains stable over time and does not exhibit, after storage for 12 months, either irreversible sedimentation or variation in the size of the nanoparticles.

EXAMPLE 15

Addition of Non-Solvent to the Solvent Phase

The method is carried out as in Example 1, but the calix[n]arene is dissolved in an tetrahydrofuran/water mixture (90/10, v/v) instead of pure tetrahydrofuran. The presence of a low proportion of non-solvent for the calix[n]arene in a solvent gives the nanospheres that are obtained, an average size of 160 nm with an average dispersion index of 0.11.

EXAMPLE 16

Stability of the Calix[n]arene Nanospheres to Ultra-Violet Irradiation

The method is carried out as in Example 1. After concentration of the suspension of calixarene nanospheres to a volume of 30 ml; the resulting suspension of calix[n]arene nanospheres is treated with ultra-violet irradiation (254 nm) for 12 hours, the size of the nanospheres after irradiation is 160 mn with an average dispersion index of 0.15. The suspension remains stable over time and does not exhibit, after storage for 12 months, either irreversible sedimentation or variation in the size of the nanospheres.

EXAMPLE 17

Preparation of Nanospheres in the Presence of a Lipophilic Active Principle

The method is carried out as in Example 1, but 5 mg of β-carotene are added to the solvent phase (2). The nanospheres obtained have an average size of 145 nm with a dispersion index of 0.12. Analysis by visible spectroscopy shows>70% incorporation of β-carotene. There is no degradation of the β-carotene over a period of storage exceeding 6 months.

EXAMPLE 18

Preparation of Nanospheres Containing Menthol

The method is carried out as in Example 1, but 10 mg of menthol are added to the organic phase. The nanospheres obtained have an average size of 100 nm and an average dispersion index of 0.14.

EXAMPLE 19

Preparation of Nanospheres in the Presence of an Amino Acid

The method is carried out as in Example 1, but 10 mg of an amino acid, for example alanine, are added to the aqueous phase. The nanospheres obtained have an average size of 130 nm and an average dispersion index of 0.12.

EXAMPLE 20

| Preparation of an aqueous gel | | |
|---|---|---|
| Phase A | Water | 84.5% |
| | Carbomer | 0.5% |
| | Propylene glycol | 15.0% |
| Phase B | Calixarene nanospheres | 0.01% to 10% |

Phase A is prepared by heating all constituents to 80° C., whereupon the mixture is homogenous. Phase B is added under vigorous stirring. The gel is forming while the mixture is cooling. The size of the nanospheres is not measured due to the viscosity of the resultant gel. However no visual sedimentation is observed after two months of storage at 4° C., 20° C. and 40° C.

The calix[n]arene based nanospheres described in this invention may be applied in a wide variety of applications, as described above.

The nanospheres of this inventions may thus be used, for example, for the following purposes:
- as modifiers of the kinetics of release of agents, such as retinal, for dermal treatment,
- as agents for the stabilization of sensitive molecules, such as β-carotene, to increase shelf life of cosmetic products,
- as agents to modify the aroma properties of cosmetic products,
- as modulators of surfactant properties of emulsifiers used in cosmetic products,
- as modulator of dermal penetration of active molecules,
- as dispersion agents for cosmetic products used in solar skin creams
- as modifiers of the pharmacokinetics of the release of active compounds such as cis-platin for the treatment of cancer,
- as agents for the stabilization of sensitive molecules such as fatty esters sensitive to lipases, in order to increase the biostability of pharmaceutical products,
- as agents for modifying the taste of orally administered medications,
- as modulators to decrease the amount of flavoring agents used in cooling processes,
- as stabilizers to increase the life time of molecules sensitive to oxidation used in the food industry,
- as controlled release systems for the liberation of orally administered medications at the pH of the stomach,
- as carriers for the selective transportation of medicines to predetermined biological sites,
- as controlled release agents for pheromones for "green" insecticide treatments.

Their use in other fields will allow to obtain similar effects. For example, the nanoparticles are miscible with lipoproteins. The plasmic membrane of living cells is an essential constituent of the structural integrity of cells. This membrane comprises lipids and proteins and acts not only as a physical barrier to separate different compartments but also as a substrate for a great number of reactions that occur in its interior.

These membrane shaped lipids are amphiphilic molecules. This affinity ambivalence provides the capability of adsorption to interfaces and the self-assembly capability in aqueous media.

The above-described nanoparticle forming calixarene derivatives, i.e. upper crown long-chain fatty acid acylated and lower crown selective phosphorylated calixarenes, especially the calix[4]arenes, show a high tendency to crystallize whereas natural phospholipids have only a low crystallizing ability. During our work, numerous crystals of the substituted calixarenes have been obtained.

The studies of Langmuir monomolecular layers have shown that our synthetic calixarenes, substituted as described above, a greatly miscible with natural phospholipids (DPPA and DPPC). The self-assemblies which are forming in water have been studied as to light diffusion dynamics and atomic force microscopy. The results show that these supramolecular assemblies are different from structures that are generally formed by lipids; in fact, the new structures are neither micelles nor liposomes (G. Gregoriadis, B. E. Ryman, Liposomes as carriers of enzymes or drugs, *Biochem. J.* 124 (1971), 58P) but nanoparticles. These nanoparticles distinguish from the above-mentioned other structures by their great mechanical resistance and their long-life stability. The new structures of this invention may therefore also be used for the solubilization of membrane proteins and for the reconstitution of biomimetic systems where the process of crystal nucleation is favored.

The invention claimed is:

1. A pharmaceutically or cosmetically acceptable dispersible colloidal composition containing nanoparticles in the shape of matrix nanospheres, each said matrix nanosphere defining a molecular cavity, said nanospheres consisting essentially of at least one amphiphilically modified calixarene and having a size of from 50 to 500 nm, wherein the nanospheres are dispersed in a continuous phase containing water, and wherein said modified calixarene has the general formula

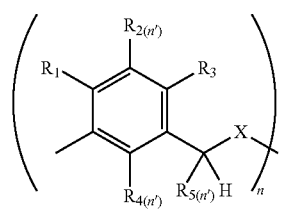

Formula 1 wherein:
R1=H, OH, OR or OCOR;
R2=H, R, COR, CH2Pol, Y or CH2Y;
R3=H, OH, OR or OCOR;
R4=H, OR, OCH2R, OCOR or an ester, carboxylic acid, amido, amino, peptide or carbohydrate group;
R5=R or Y; R=a saturated or unsaturated straight or branched hydrocarbon chain that may be substituted by halogen and/or by a group Pol; or R is a cyclic hydrocarbon radical, saturated or not;
Pol=a polar group selected from phosphoric acid, sulfuric acid, amino, ammonium, carboxylic acid and their salts;
Y=halogen or pseudo-halogen;
X=a direct bond, 0, S or NR6R7
R6=alkyl
R7=alkyl
n=an integer of from 3 to 20; and
n'=an integer≦n;
the compound of the above formula containing at least one group Pol.

2. A pharmaceutically or cosmetically acceptable dispersible colloidal composition containing nanoparticles as a carrier in the shape of matrix nanospheres, each said matrix nanosphere defining a molecular cavity, said nanospheres consisting essentially of at least one amphiphilically modified calixarene and having a size of from 50 to 500 nm wherein active molecules to be carried are included within the cavity defined in each said matrix nanosphere and said nanospheres are dispersed in a continuous phase containing water, and wherein said modified calixarene has the general formula

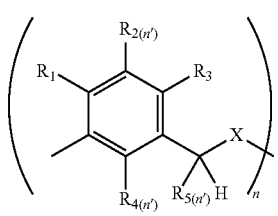

Formula 1 wherein:
RI=H, OH, OR or OCOR;
R2=H, R, COR, CH2Pol, Y or CH2Y;
R3=H, OH, OR or OCOR;
R4=H, OR, OCH2R, OCOR or an ester, carboxylic acid, amido, amino, peptide or carbohydrate group;
R5=R or Y; R=a saturated or unsaturated straight or branched hydrocarbon chain that may be substituted by halogen and/or by a group Pol; or R is a cyclic hydrocarbon radical, saturated or not;
Pol=a polar group selected from phosphoric acid, sulfuric acid, amino, ammonium, carboxylic acid and their salts;
Y=halogen or pseudo-halogen;
X=a direct bond, 0, S or NR6R7
R6=allcyl
R7=alkyl
n=an integer of from 3 to 20; and
n'=an integer≦n;
the compound of the above formula containing at least one group Pol.

3. The dispersible colloidal composition of claim 2, wherein both said nanospheres and said continuous water-containing phase contain at least one active substance.

4. The dispersible colloidal composition of claim 2, wherein said active substance is a cosmetically used compound or composition.

5. The dispersible colloidal composition of claim 2, wherein said active substance is a pharmaceutically used compound or composition.

6. The dispersible colloidal composition of claim 2, wherein said active substance is a nutritionally used compound or composition.

7. The dispersible colloidal composition of claim 2, wherein said active substance is a compound or composition used for phytosanitary purposes.

8. The dispersible colloidal composition of claim 1 wherein said modified calixarene is selected from the group consisting of tetra-p-acyl-calix [4] arenes, tetra-p-acyl-calix [6] arenes and tetra-p-acyl-calix [8] arenes, wherein acyl is the acyl residue of a carboxylic acid having from 8 to 16 carbon atoms.

9. A process for the preparation of a pharmaceutically or cosmetically acceptable dispersible colloidal composition according to claim 1, characterized by the following steps:
(1) providing at least one amphiphilic substituted calixarene;
(2) providing a liquid phase consisting essentially of a solution of said amphiphilic calixarene in an organic solvent;
(3) providing a second liquid phase consisting of water or an aqueous mixture or ionic solution;
(4) combining said two liquid phases of steps (2) and (3); and
(5) recovering a colloidal suspension of nanospheres consisting essentially of said amphiphilically substituted calixarene.

10. The process according to claim 9, wherein the volume ratio of the first liquid phase (2) to the second liquid phase (3) is from 0.1 to 1000.

11. The process according to claim 9, further comprising removing all or part of the organic solvent, and removing all of the water or aqueous mixture thereby obtaining a nanosphere powder.

12. The process according to claim 11, wherein all of the water is removed by freeze-drying.

13. The process according to claim 9, further comprising adjusting the concentration of the colloidal suspension obtained in step (4) by removing a part of the organic solvent, and by removing a part of the water or aqueous mixture, or by the adjunction of further aqueous phase, either pure or in the form of a solution.

14. The process according to claim 9, further comprising incorporating said colloidal suspension recovered in step (5) into a gel or an emulsion.

15. A process for the preparation of a dispersible colloidal composition according to claim 1, characterized by the following steps: providing at least one amphiphilic substituted calixarene:
(1) providing a liquid phase containing a solution of said amphiphilic calixarene in an organic solvent;
(2) providing a second liquid phase containing water or an aqueous mixture or ionic solution, wherein at least one of said liquid phases includes a non-ionic or an ionic surfactant,
(3) combining the two liquid phases of steps (2) and (3); and
(4) recovering a colloidal suspension of nanospheres consisting essentially of said amphiphilically substituted calixarene.

16. The process according to claim 15, wherein the surfactant is present in a proportion of from 0.1 to 50% by weight of the colloidal suspension recovered in step (5).

17. A process for the preparation of a pharmaceutically or cosmetically acceptable dispersible colloidal composition according to claim 1, characterized by the following steps:
(1) providing at least one amphiphilic substituted calixarene;
(2) providing a first liquid phase consisting essentially of a solution of said amphiphilic calixarene in an organic solvent;
(3) providing a second liquid phase consisting of water or an aqueous mixture or ionic solution
wherein one or more active molecules are included in at least one of said first and second liquid phases,
(4) combining the first and the second liquid phases; and
(5) recovering a colloidal suspension of nanospheres consisting essentially of the amphiphilically substituted calixarene, wherein the at least one active molecule is contained within a molecular cavity in each said nanosphere or, in addition, within a continuous water-containing phase in which said nanospheres are dispersed.

18. The process according to claim 17, wherein said active substance is a cosmetically used compound or composition.

19. The process according to claim 17, wherein said active substance is a pharmaceutically used compound or composition.

20. The process according to claim 17, wherein said active substance is a nutritionally used compound or composition.

21. The process according to claim 17, wherein said active substance is a compound or composition used for phytosanitary purposes.

* * * * *

UNITED STATES PATENT AND TRADEMARK OFFICE
CERTIFICATE OF CORRECTION

| | | |
|---|---|---|
| PATENT NO. | : 7,943,175 B2 | Page 1 of 1 |
| APPLICATION NO. | : 10/489894 | |
| DATED | : May 17, 2011 | |
| INVENTOR(S) | : Anthony Coleman et al. | |

It is certified that error appears in the above-identified patent and that said Letters Patent is hereby corrected as shown below:

Cover Page

Item (73) Assignee should read:

NanoPart S.A. (CH)

Signed and Sealed this
Twenty-eighth Day of June, 2011

David J. Kappos
*Director of the United States Patent and Trademark Office*